US00PP18956P2

(12) United States Plant Patent
Jansen

(10) Patent No.: US PP18,956 P2
(45) Date of Patent: Jun. 17, 2008

(54) ***TRICYRTIS* PLANT NAMED 'IMPERIAL BANNER'**

(50) Latin Name: ***Tricyrtis* sp.**
Varietal Denomination: Imperial Banner

(75) Inventor: Robert D. Jansen, Beaverton, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 3 days.

(21) Appl. No.: 11/637,318

(22) Filed: Dec. 11, 2006

(51) Int. Cl.
*A01H 5/00* (2006.01)

(52) U.S. Cl. ..... Plt./488; Plt./263.1

(58) Field of Classification Search ..... Plt./488
See application file for complete search history.

(56) References Cited

PUBLICATIONS

Internet websire: https://wwwplantdelights.com/Catalog/Current/page98.html (7 pages total).*
Internet website: http://www.crug–farm.co.uk/plantlist.asp?id+1103 (1 page).*

* cited by examiner

*Primary Examiner*—Kent Bell
*Assistant Examiner*—S. B. McCormick-Ewoldt
(74) *Attorney, Agent, or Firm*—Klarquist Sparkman, LLP

(57) ABSTRACT

A new and distinct *Tricyrtis* plant characterized by its unique, white-variegated foliage, compact, upright habit, and large purple spotted flowers.

1 Drawing Sheet

Botanical denomination: *Tricyrtis* sp.
Variety designation: 'Imperial Banner'.

BACKGROUND OF THE INVENTION

The present invention relates to a new and distinct *Tricyrtis,* and given the cultivar name is 'Imperial Banner'. *Tricyrtis* is in the family Liliaceae. The plant is mutation of *Tricyrtis* 'Empress' (not patented). It was found in tissue cultured material in Canby, Oreg.

SUMMARY OF THE INVENTION

This new cultivar unique and characterized by:

1. Unique, white-variegated foliage
2. Compact, upright habit
3. Large purple spotted flowers This new cultivar has been reproduced only by asexual propagation (division and tissue culture). Each of the progeny exhibits identical characteristics to the new cultivar. Asexual propagation by tissue culture using standard micropropagation techniques with lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows the flower and flower bud of a three year old *Tricyrtis* 'Imperial Banner' taken in July and growing in a two gallon container in the shade house in Canby, Oreg.

FIG. 2 shows the foliage of a 2 year old plant growing in a two gallon container in the shade house in Canby, Oreg.

DETAILED PLANT DESCRIPTION

The following is a detailed description of the new *Tricyrtis* cultivar based on observations of a three year old specimen grown in a two gallon pot in an open air shade house with 50% shade in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 6 to 9.
- *Size.*—Grows to 30 cm wide and 60 cm tall from the top of the soil to the top of the inflorescence.
- *Form.*—With short rhizomes forming a compact clump.

Stem:
- *Type.*—Branched, erect stems.
- *Size.*—Main stem 20 to 60 cm long and 2 to 4 mm wide, laterals grow to 20 cm long and 2 mm wide.
- *Surface texture.*—Pubescent.
- *Stem number.*—22.
- *Number of leaves per stem.*—3 to 10 main stem leaves with leafy flowering branches from each.
- *Internode length.*—1 to 6.5 cm.
- *Color.*—Yellow Green 152B (to Greyed Brown 199B at base on large stems).

Leaf:
- *Type.*—Simple.
- *Shape.*—Elliptic to narrowly elliptic.
- *Arrangement.*—Alternate.
- *Blade length.*—Grows to 10.5 cm.
- *Blade width.*—Grows to 3.5 cm.
- *Margins.*—Entire, pubescent, and strongly undulating.
- *Apex.*—Cuspidate and curling.
- *Base.*—Clasping.

*Texture.*—Leathery.

*Surface texture.*—Glabrous on upper surface, bottom surface is pubescent on main veins.

*Venation.*—Parallel.

*Color.*—Topside: margins and centers Green 137A, banded Yellow 4D between the main veins with stronger variegation on top most leaves. Bottom side; Green 137B, banded Yellow 4D.

Inflorescence:

*Type.*—Axillary.

*Number of flowers per stem.*—56 on a 60 cm stem.

*Number of flowers per cyme.*—1 to 5 for axillary cyme and 1 to 13 for a terminal cyme.

*Pedicel description.*—Grows from 1 to 2 cm long, pubescent, Yellow Green 148A.

*Bloom time.*—August to October in Canby, Oreg.

Flower bud:

*Size.*—1.6 cm long and 5 mm wide.

*Shape.*—Oblong, narrowing above the base.

*Surface texture.*—Pubescent.

*Color.*—Greyed Yellow 162D at the bottom ⅓ changing to Greyed Purple 187B on the top ⅓ with the tips Greyed Purple 187A.

Flower:

*Type.*—Actinomorphic, up facing, with segments free.

*Shape.*—Stellate.

*Size.*—Grows to 2.5 cm deep and 3.8 cm wide.

*Texture.*—Waxy.

*Surface texture.*—Glabrous inside, pubescent outside.

*Color.*—White 155A with large 1 mm oval spots of Red Purple 71A.

*Corolla description.*—6 tepals, oblong, entire, reflexed, 2.6 cm long and 5 mm wide, acute, outer tepals with saccate spur at the base.

*Pistil description.*—2.3 cm. long, ovary 2.3 cm long and Yellow Green 145A, style 5 mm long, White 155A with spots of Red Purple 71A, stigma 3-parted, bifid at the tips, glandular, each branch is 7 mm long and colored White 155A with spots of Red Purple 71A.

*Stamen.*—6, filaments 2.4 cm long, White 155A with spots of Red Purple 71A, anthers 2.5 mm long and Greyed Purple 187A, male sterile, no pollen produced.

*Fragrance.*—None.

Fruit:

*Type.*—Capsule.

*Size.*—2 cm long and 3 mm wide.

*Shape.*—Narrowly oblong, 3 angled.

*Color.*—Yellow Green 144D.

Seed: None produced, sterile.

Pest and diseases: Snail and slugs are the main problems on *Tricyrtis*. This new cultivar has leathery waxy leaves and appears to be less appealing to slugs. No other problems have been observed on plant grown under commercial conditions in Canby, Oreg.

COMPARISONS TO SIMILAR *TRICYRTIS*

Compared to the other variegated *Tricyrtis* on the market, *Tricyrtis* 'Imperial Banner' has the narrow leaf and short compact habit of *Tricyrtis* 'Empress' combined with a variegation color of cream and deep green and a variegation pattern that goes to the middle of the leaf rather than only on the leaf edges.

Compared to the parent *Tricyrtis* 'Empress' this new variety has smaller more undulating leaves and strong variegation.

I claim:

1. A new and distinct hybrid *Tricyrtis* plant as herein shown and described.

* * * * *

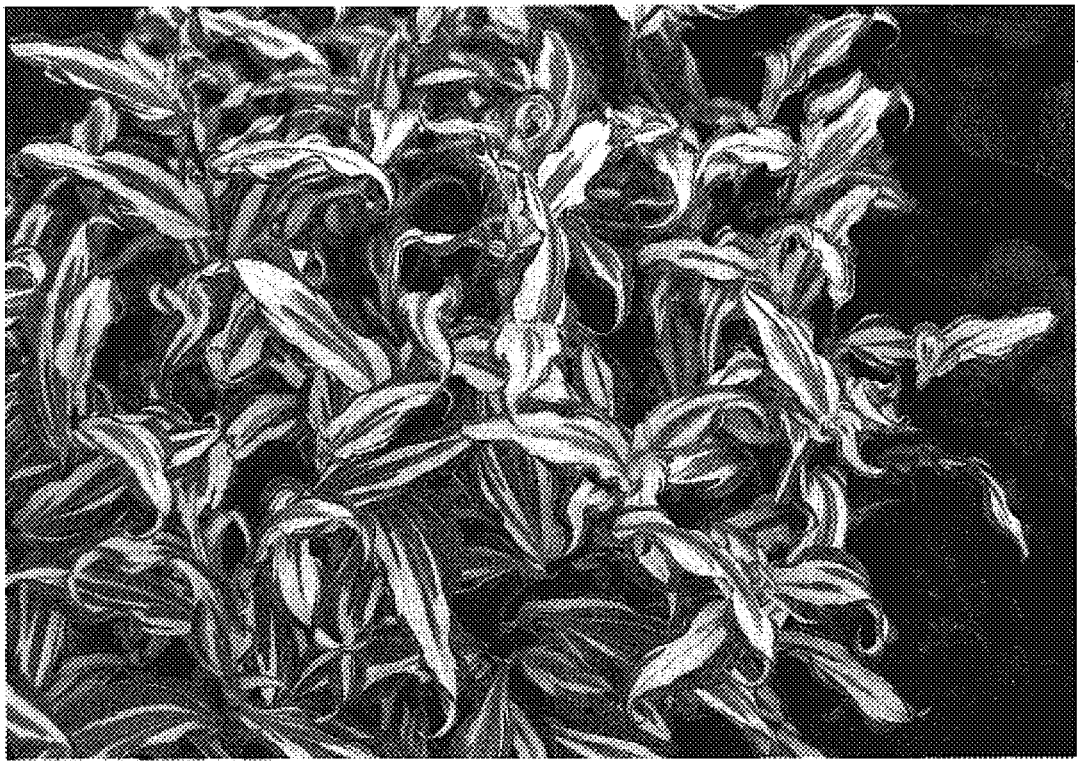

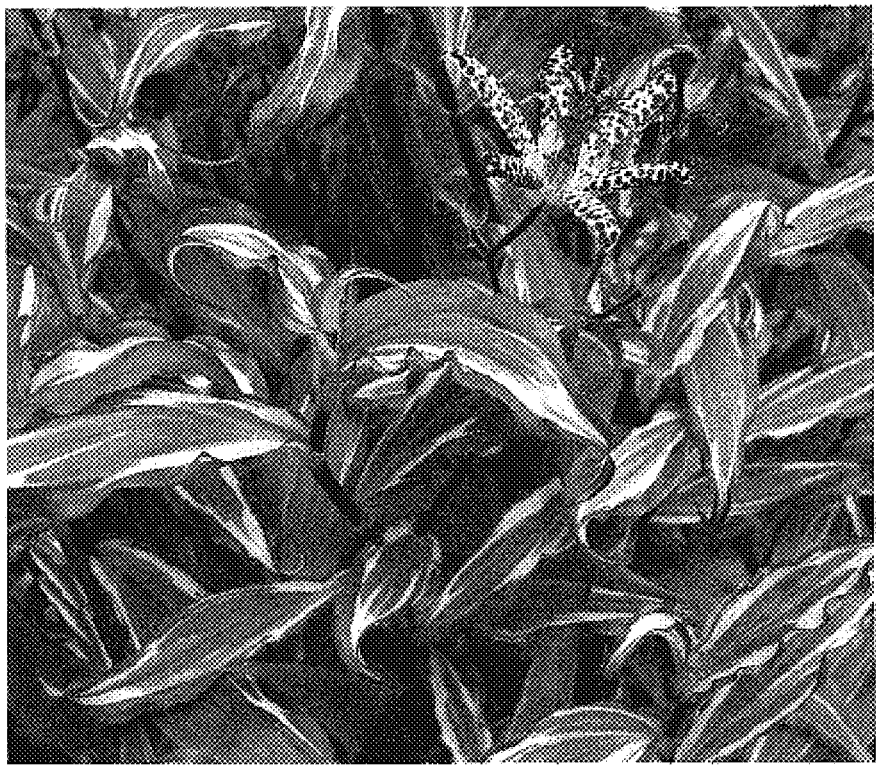
Figure 1 above, figure 2 below.